United States Patent [19]
Arter et al.

[11] Patent Number: 6,046,052
[45] Date of Patent: Apr. 4, 2000

[54] DRY ANALYTICAL ELEMENTS FOR THE DETERMINATION OF PROTEIN

[75] Inventors: Thomas Arter; David B. LaTart; John C. Mauck; Richard C. Sutton, all of Rochester; Wayne Weber, Mendon; Robert Winterkorn, Rochester; James Schaeffer, Penfield, all of N.Y.

[73] Assignee: Ortho Clinical Diagnostics, Inc., Rochester, N.J.

[21] Appl. No.: 09/065,930

[22] Filed: Apr. 24, 1998

Related U.S. Application Data

[60] Provisional application No. 60/045,754, May 6, 1997.
[51] Int. Cl.$^7$ .................................................. G01N 33/48
[52] U.S. Cl. ........................ 436/86; 436/169; 436/170; 422/56
[58] Field of Search .................... 422/56, 57; 436/86, 436/164, 169, 170, 175

[56] References Cited

U.S. PATENT DOCUMENTS

| | | | |
|---|---|---|---|
| 5,087,575 | 2/1992 | Lau | 436/166 |
| 5,149,416 | 9/1992 | Osterhoudt et al. | 204/456 |
| 5,399,498 | 3/1995 | Pugia | 436/86 |

OTHER PUBLICATIONS

CAPLUS abstract of Marshall et al. ("Protein contration by precipitation with pyrogallol red prior to electrophoresis", Electrophoresis (Jul. 1995), 16(1), 28–31).

*Primary Examiner*—Jill Warden
*Assistant Examiner*—Alex Noguerda
*Attorney, Agent, or Firm*—Todd Volyn; James Harrington; Charles Limuti

[57] ABSTRACT

A dry analytical element is disclosed which can be used to sensitively and rapidly detect and quantitate protein. The assays are carried out using a dye that reacts with protein and molybdate ion to produce a measurable change in the spectral absorption of the dye. Also disclosed are polymers which stabilize and enhance the accuracy of the assay, and compounds which reduce interference by bicarbonate.

36 Claims, No Drawings

DRY ANALYTICAL ELEMENTS FOR THE DETERMINATION OF PROTEIN

This application claims priority from provisional application Ser. No. 60/045,754, filed May 6, 1997.

FIELD OF THE INVENTION

The present invention relates to dry analytical elements and methods for using the same to quantitate protein in fluid samples. More particularly, the present invention relates to the use of particular dyes and molybdate ion, polymers comprising acrylamide and hydroxycarboxylic acids in such analytical elements.

BACKGROUND OF THE INVENTION

There is a continuing need in medical practice and research, and in analytical and diagnostic procedures for rapid and accurate determinations of chemical and biological substances which are present in various fluids, such as biological fluids. For example, the presence and quantity of protein must be determined rapidly and accurately for effective research, diagnosis and treatment of many human diseases.

A wide variety of analytical methods have been developed in recent decades to detect the noted substances. The methods have become highly reliable and in some instances, suitable for automation, as well as suitable for use in kit form.

Protein assays have been traditionally carried out in solution, or in test devices where fluids are removed in some fashion from the reagents participating in the assay. Although solution techniques have enjoyed broad acceptance in this area, they typically require analyzer equipment often having intricate solution handling and transport capabilities. Moreover, the analytical equipment used in such assays can involve complex liquid handling, and may require skilled personnel, both for operation and the precise cleaning that may be needed to avoid sample to sample contamination.

An alternative to solution chemistry is the use of dry analytical elements. It should be understood that not all solution-based analytical assays can be adapted for use in dry analytical elements because of interference from coating agents, such as binders, surfactants, and other reagents necessary to promote or facilitate material deposition, sample wetting, and maintain structural integrity of said elements. Moreover, dry analytical elements must use in situ compartmentalization to segregate incompatible components. Such is not the case in solution chemistry where separate liquid storage and successive liquid additions can be employed.

Dry analytical elements and their use are described in numerous publications, including U.S. Pat. No. 4,132,528, U.S. Pat. No. 4,786,605, U.S. Pat. No. 3,992,158, U.S. Pat. No. 4,258,001 to Pierce et al., U.S. Pat. No. 4,670,381 to Frickey et al., WO 82/2601 (published Aug. 5, 1982), European Patent Application No. 051 183 (published May 12, 1982) and European Patent Application No. 066 648 (published Dec. 15, 1982). The entire contents of the noted citations are incorporated herein by reference.

A useful diagnostic indicator for assessing and monitoring patient kidney function is the total protein concentration present in urine. The nature and amount of protein present in urine is varied and dependent on the particular disease state which results in the failure of the kidney to prevent passage of proteins into the urine.

Examples of proteins that may be found in urine include, but are not limited to, albumin, intact immunoglobulins, kappa free-chains, lambda free-chains, retinol binding protein, alpha-l-microglobulin, and beta-l-microglobulin. These proteins differ widely in amino acid composition and molecular weight. The information of interest to the clinician using a urine total protein screening assay is the total mass of protein per unit volume of the urine specimen. The diagnostic assay, that is, the measured signal ideally, should be independent of the nature or type of proteins that may be present. For example, 50 mg/dL of albumin should produce the same signal as 50 mg/dL of any other protein. The normal protein concentration range in human urine is between approximately 5 to 100 mg/dL.

Various means have been used to determine the total protein concentration in biological materials. In many analytical assays, an optical signal, such as absorption in the visible or ultraviolet region of the spectrum, is measured which is proportional to the concentration of protein in the sample. Generally, however, the signal is undesirably a function of the nature of the protein in the sample and not simply related to the mass of protein present. These methods usually rely on one of the following means to generate a detectable optical signal:

1. A complex of protein and Cu(II), the biuret reaction, results in a detectable but small absorption in the visible region of the spectrum.

2. Absorption in the ultraviolet region of the spectrum by aromatic amino acids of the protein may be measured.

3. The amount of protein may be determined by derivitization of specific amino acids with molecules containing chromophores which may be quantified using their intrinsic absorption or fluorescence.

4. Dyes which can bind to protein noncovalently to generate a dye-protein complex resulting in a perturbation of the dye's absorption spectrum may be used to determine the presence or amount of protein in a sample. Some dyes require the presence of a metal ion, such as molybdenum, or tungsten in which case formation of a noncovalent complex of dye, metal ion, and protein results in the perturbation of the dye's absorption spectrum which may be used to determine the presence or amount of protein in a sample.

5. The competition of protein with a dye for coordination of Cu(II) results in an absorption signal that is proportional to the protein concentration(the Cu(II)/dye coordination complex has a different absorption spectrum from that of free dye, that is, dye which is not coordinated to Cu(II)).

U.S. Pat. No. 4,132,528 relates to assays for protein based on the biuret reaction. Dry assay elements of the '528 patent comprise a biuret reagent of CU(II) and a chelating agent therefore, e.g., $CuSO_4$ and tartaric acid, or a complex of the two, and a buffer that provides a pH above about 12. When protein in an aqueous fluid, such as serum or cerebral spinal fluid (CSF), interacts with the biuret reagent at a pH above 12, a reaction between the cupric form of copper and the protein occurs to produce a violet color. The intensity of the color is directly proportional to the protein content of the serum, and the protein level can be measured by well known calorimetric analytical techniques. Unfortunately, the dry slide elements of the noted patent have lower sensitivity than desired, i.e., they cannot detect protein levels at or below about 200 mg/dL.

U.S. Pat. No. 4,786,605 describes dry analytical element formulations for quantification of protein having greater sensitivity than the elements of the '528 patent by replacing the biuret reagent(s) with a preformed Cu(II)/pyridylazo dye coordination complex (or free Cu(II) and free pyridylazo dye). When aqueous protein is added to the assay element cupric ion is displaced from the complex by the protein, and the absorption curve of the Cu(II)/dye complex is shifted to the absorption curve of the uncoordinated dye. Therefore, upon addition of protein, the absorption peak of the Cu(II)/dye complex is reduced in proportion to the amount of protein added, and from suitable calibration with samples having a known concentration of protein, an unknown concentration of protein in a liquid sample can be determined calorimetrically. The patent teaches that those elements have very good dynamic range and sensitivities as much as about 30 times greater than elements based on the biuret reaction.

The use of the '605 patent technology to quantify protein in urine samples, however, consistently shows that about 10 to 20% of the urine samples exhibit an unacceptable random positive bias compared with values obtained using a Coomassie Blue solution assay for protein concentration as the reference standard, i.e., the estimated protein concentration of certain patient urine samples (about 10 to 20% of the sample population), using the '605 patent technology, is greater than that determined using the Coomassie Blue-based assay method. It was deduced that this random positive bias was caused by the presence, in certain urine samples, of reducing agents such as ascorbic acid which cause the reduction of both Cu(II) and reducible groups on the dye such as nitro groups. A dry analytical element is desired which is not susceptible to the deficiencies of the aforementioned assay methodologies.

The reaction, in solution, of particular indicator dyes in complexation with protein and metal ions under acidic conditions which yields a measurable color change is well known. As mentioned above, an analytical assay method which works well in solution may not be readily adapted to dry analytical elements for reasons cited therein.

It is highly desirable that different proteins react equally with a dye to produce an optical signal which is related to the mass of protein present in the sample and independent of the nature of the protein. Urine contains variable quantities of bicarbonate (up to about 200 mM). High levels of bicarbonate in a urine specimen, if not diluted out or removed by sample pretreatment (such as by molecular size exclusion techniques), can introduce sufficient bicarbonate into the assay to produce very alkaline conditions which may render the assay unreliable or useless, since the dye-metal ion-protein interaction takes place at a low pH (1.5 to 3.5) and/or bicarbonate may interfere, additionally, through coordination of the metal ion. A need exists to provide dry analytical elements for the determination of protein which are not susceptible to the presence of reductants or bicarbonate, which produces a signal measurement that correlates substantially with the mass of protein present, that is, a signal measurement which is substantially (wherein substantially means suitable or acceptable for the specific protein measurement application, such as a measure of total protein in urine samples) independent of the nature of the protein, and can be used to quantitate protein in a range between approximately 5 to approximately 300 mg/dL and does not require predilution, preconcentration, or pretreatment of the sample to remove said interferents.

Unexpectedly, it has been found that dry analytical elements comprising indicator dyes in the presence of molybdate ion together with polymers comprising acrylamide, and hydroxycarboxylic acid compounds can be prepared which are suitable for use in is determining the amount or presence of protein in biological fluids.

SUMMARY OF THE INVENTION

The problems of the prior art dry analytical elements for determining protein concentration have been overcome using indicator dyes in the presence of molybdate ion in combination with acrylamide polymers and hydroxycarboxylic acid compounds in dry analytical elements of the present invention. Molybdate ion is the preferred metal ion for embodiments of the present invention. However, the embodiments of the present invention are not limited to just molybdate ion. Other suitable metal ions, such as tungstate ion, also are considered to be within the scope of the present invention.

It is highly desirable, as stated above, that different proteins react equally with the dye to produce an optical signal which is related to the mass of protein present in the sample and is independent of the nature of the protein. It has been found, unexpectedly, that the polymer vehicle used to coat various reagents of the dry element affects the apparent reactivity of the indicator dye system with different proteins. Thus, the magnitude of the measured optical signal is dependent on the nature or type of protein present; however, this dependence on the type of protein is significantly reduced when polymers comprising acrylamide are present in the dry analytical elements.

A dry analytical element for the quantitation of total protein in a sample is disclosed herein based on measuring the change in reflection density at an appropriate wavelength upon formation of a complex of indicator dye with protein in the presence of ammonium molybdate. The dry element of this invention is useful in determining the amount of protein in any liquid sample, in particular biological fluids.

More specifically, in one embodiment, the present invention relates to a dry analytical element useful for the determination and quantitation of protein comprising:

(i) a porous spreading layer,
(ii) one or more additional layers which are in fluid contact with the porous spreading layer, and
(iii) a support,
wherein said element contains, in at least one of the layers, a polymer comprising arcrylamide, indicator dye and molybdate ion which react to produce a measurable change in the spectral absorption or reflection density of the dye upon contact of said element with a fluid suspected of comprising protein, and wherein said dye, said molybdate salt and said polymer comprising acrylamide may be present together in the same layer or be present in any combination or individually in separate layers of said element.

The present invention provides a method for using the above dry analytical element in the determination and quantitation of a protein, comprising:

(A) adding a hydoxycarboxylic acid having the formula,

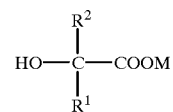

wherein $R^1$ and $R^2$ are independently H, —CH$_3$, —CH$_2$CH$_3$ or —CH$_2$OH and M is H, or a positively charged metal or non-metal counterion, to a fluid sample suspected of containing protein;

(B) contacting the fluid sample comprising the hydroxycarboxylic acid with said analytical element; and (C) measuring the change in spectral absorption or reflection density of the dye as a measure of the presence and amount of protein.

In a preferred embodiment, the present invention relates to an analytical element useful for the determination and quantitation of protein comprising:

(i) a porous spreading layer, (ii) one or more additional layers which are in fluid contact with the porous spreading layer, and (iii) a support, wherein said element contains, in at least one of the layers, a polymer comprising arcrylamide, and wherein said element comprises a hydroxycarboxylic acid, having the formula,

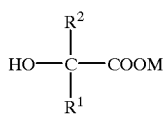

wherein $R^1$ and $R^2$ are independently H, —$CH_3$, —$CH_2CH_3$ or —$CH_2OH$ and M is H, or a positively charged metal or non-metal counterion, and further comprises an indicator dye and molybdate ion which react to produce a measurable change in the spectral absorption or reflection density of the dye upon contact of said element with a fluid suspected of comprising protein and wherein said dye, said molybdate salt, said polymer comprising acrylamide and said hydroxycarboxylic acid may be present together in the same layer or be present in any combination or individually in separate layers of said element.

The present invention provides a method for using the above preferred dry analytical element in the determination and quantitation of a protein, comprising:

(A) contacting a fluid sample suspected of containing protein with said analytical element;

(B) measuring the change in spectral absorption or reflection density as measure of the presence and amount of protein.

DETAILED DESCRIPTION OF THE INVENTION

The present invention is used advantageously to determine the presence and/or concentration of protein in various aqueous fluids, such as human and animal biological fluids, foods, industrial or municipal effluents, and other fluids commonly tested in this manner. Biological fluids which can be tested include, but are not limited to, whole blood, serum, plasma, urine, spinal fluid, lacrimal fluid, synovial fluid, lymphatic fluid, suspensions of tissues or plaque, gingival fluid, vaginal fluid, cranial fluid and other fluids readily apparent to one skilled in the art.

Proteins which can be determined include, but are not limited to, peptides, polypeptides, proteins (such as enzymes, antibodies, lipoproteins and glycoproteins), and compounds which contain or are attached to (covalently or noncovalently) peptides, polypeptides and/or proteins. The present invention is particularly useful in the determination of protein in urine.

The present invention is carried out using an analytical element comprising a porous spreading layer, usually a coated layer which has suitable porosity for accommodating a test sample (for example 1 to 50 μL), diluted or undiluted.

The element of the present invention is assembled using techniques that are well known in the art. Preferably, the porous spreading layer is isotropically porous, which property is provided by interconnected spaces among the particles, fibers or other physical components of the layer. By isotropically porous is meant that fluids are uniformly spread throughout the layer. Useful materials for such layers are water-insoluble and maintain their structural integrity during the assay. Conventional materials and means for assembling the element are described, for example, in U.S. Pat. No. 3,992,158 to Przybylowicz et al., U.S. Pat. No. 4,258,001 to Pierce et al., U.S. Pat. No. 4,292,272 to Kitazima et al. and U.S. Pat. No. 4,430,436 to Koyama et al., the entire contents of which are incorporated herein by reference. The preferred porous spreading layers are prepared from barium sulfate in ESTANE as described in U.S. Pat. No. 3,992,158 to Przybylowicz et al.

There are one or more additional layers in the element, all of which are in fluid contact with the porous spreading layer. It should be understood that the term "fluid contact" is used herein to denote that fluids can readily move from one layer to another. Such additional layers, preferably coated polymer layers, include sub, reagent, and radiation blocking layers and are composed of one or more hydrophilic binder materials as are known in the art, such as gelatin, and vinylpyrrolidone polymers. Some layers may be water-insoluble while others may be water-soluble.

The layers of the element of the present invention can be self-supporting, but preferably, these layers are disposed on a suitable dimensionally stable, chemically inert support. Preferably, the support is nonporous and transparent to electromagnetic radiation. A support of choice should be compatible with the intended mode of detection (for example, transmission or reflectance spectroscopy). Useful support materials include, but are not limited to, paper, metal foils, polystyrenes, polyesters, polycarbonates and cellulose esters.

In at least one of the layers of the element of this invention is a dye which is capable of specifically reacting with protein and molybdate ion.

As used herein, "a dye which reacts with protein and molybdate ion" is meant to be any dye compound for which the spectral or optical absorption properties of the dye in the presence of molybdate ion and protein is altered from that of the dye and molybdate ion in the absence of protein. Dyes having the desired aforementioned characteristics include those comprising open aromatic structures and tricyclic aromatic structures having functional groups (such as, but not limited to, two adjacent hydroxyl groups on an aromatic ring) which groups are capable of coordinating molybdate ion. Such dyes include but are not limited to pyrocatechol violet, tetrabromophenolphthalein ethyl ester, triiodophenolsulfonphthalein, tetrabromopyrogallol red, and pyrogallol red.

In a preferred embodiment of this invention, a multilayer analytical element for the determination of the presence and/or amount of protein is provided. Specifically, the multilayer element comprises a nonporous support having thereon, in fluid contact:

(i) a first reagent or buffer layer, comprising a dye which reacts with protein and molybdate ion, a molybdate salt, a polymer comprising acrylamide, (ii) a sub layer, and (iii) a porous spreading layer.

The elements of this invention can include a variety of additives in appropriate layers as are known in the art to aid in manufacture, fluid spreading, and absorption of unwanted radiation.

The element of the present invention can be prepared using conventional coating procedures and equipment as are described in the prior art (including gravure, curtain, hopper and other coating techniques). The elements can be configured in a variety of forms, including elongated tapes of any desired width, sheets, slides or chips. Further, the method of this invention can be manual or automated using appropriate analytical equipment and procedures. Generally, the method includes contacting the reagents in the element by spotting a test sample (for example, 1 to 50 µl) on the porous spreading layer. The movement of fluid within the element effectively mixes the reagents for the reactions to take place.

After sample application, the element is exposed to any conditioning, such as incubation, heating or other procedure, that may be desirable to quicken or otherwise facilitate forming the protein-dye-molybdate complex.

Dyes which react with protein and molybdate ion employed in the instant invention, as indicated above, include but are not limited to those comprising open aromatic structures and tricyclic aromatic structures having functional groups (such as, but not limited to, two adjacent hydroxyl groups on an aromatic ring) which groups are capable of coordinating molybdate ion. Such dyes include but are not limited to pyrocatechol violet, tetrabromophenolphthalein ethyl ester, triiodophenolsulfonphthalein, tetrabromopyrogallol red, and pyrogallol red.

The dye compounds identified above can be obtained commercially from well known chemical suppliers such as Eastman Organic Chemical Company, Aldrich Chemical Company, Sigma Chemical Company and the like, or may be prepared using conventional starting materials and procedures well known to those skilled in the art.

Dry analytical elements separately comprising the following indicator dyes were prepared: pyrocatechol violet (pyrocatechol, 4,4'-(3H-2, 1-benzoxathiol-3-ylidine)-di-S,S-dioxide), pyrogallol red (2-(4,5,6-trihydroxy-3-oxo-3H-xanthen-9-yl) benzenesulfonic acid), bromopyrogallol red (spiro[3H-2, 1-benzoxathiol-3',9'-[9H]-xanthen-3',4',5',6'-tetrol-2,7-dibromo-I,I-dioxide]), gallein (3',4',5',6'-tetrahydroxyspiro[isobenzofuran-1 (3H),9'-[9H]xanthen]-3-one). General features of dry analytical elements are described in U.S. Pat. No. 3,992,158 to Przybylowicz et al. and in U.S. Pat. No. 4,258,001 to Frank and Pierce. All the dyes are sensitive to physico-chemical environmental changes.

We have found that quantitative analysis of urine protein can be carried out using the above-identified dyes in combination with molybdate ion in dry analytical elements. Dry analytical elements comprising pyrocatechol violet in combination with molybdate ion provided the best analytical detection sensitivity (that is, the best change in reflection density, Dr, over the desired protein concentration range, up to 300 mg/dL) and replicate precision with prepared solutions comprising human albumin.

We have found, unexpectedly, that the polymer vehicle used in coating various reagents of the dry element affects the apparent reactivity of the indicator dye system with different proteins, and thus, the dependence of the magnitude of the measured optical signal with respect to the type of protein present. Polymers suitable for use in the present invention act to level the optical signal, that is, the polymer acts to reduce the difference in the measured reflectance density signal obtained with equivalent masses or weights of different proteins. This is desirable since different protein types may predominate in different specimens and the desired measure is the total mass of protein present per unit volume of sample (total protein). Ideally, an assay for total protein should quantitate all proteins with equal sensitivity. The polymers of the present invention include, but are not limited to, water-soluble homopolymers, co-polymers and ter-polymers, comprising mostly (greater than about 40 weight percent) acrylamide. Functional groups which can coordinate molybdate ion, if present in the polymers of this invention, must not be present in an amount that interferes with determination of protein. A preferred polymer is a homopolymer of acrylamide, that is, polyacrylamide (hereinafter referred to as polyA) having a weight average molecular mass between approximately 20,000 and 250,000 daltons. The most preferred range is between approximately 100,000 and 150,000 daltons.

Additionally, we have found, quite unexpectedly, that adding glycolic acid to the multilayer analytical element preferably, precoated in the element) substantially reduced interference due to bicarbonate. Other hydroxycarboxylic acids having the general structural formula:

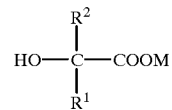

wherein $R^1$ and $R^2$ are independently H, —$CH_3$, —$CH_2CH_3$ or —$CH_2OH$, and M is H, or a positively charged metal or non-metal counterion, have a similar effect and are suitable for use in the present invention. Representative hydroxycarboxylic acids having the above formula include 2-hydroxypropanoic acid, 2-methyl-2-hydroxyprpanoic acid and salts thereof.

A satisfactory quantitative analysis of urine protein can be obtained using dry analytical elements comprising indicator dyes and molybdate ion in combination with the noted acrylamide polymers and hydroxycarboxylic acids. Pyrocatechol violet with molybdate ion in combination with a polyacrylamide polymer, said polyacrylamide polymer having a molecular mass of between approximately 20,000 and 250,000 daltons and also in combination with glycolic acid is a preferred dry analytical element, providing a sensitive measure of protein concentration up to 300 mg/dL and very good replicate precision. A most preferred dry element comprises polyA (having an average molecular mass of between 100,000 and 150,000 dalatons) as polymer vehicle coated in a reagent/buffer layer and pre-coated glycolic acid.

Polyacrylamide acts to level the reactivity of the indicator dye pyrocatechol violet/molybdate ion system with different proteins. The difference in the reflectance density signals for the same mass concentration of different protein types is reduced significantly in dry elements using the preferred polymer. The effect of the polymer using pyrocatechol violet and molybdate is observed using other types of indicator dyes and metal-ions. This invention allows the preparation of a dry element for the quantitation of total protein in urine, having a range of between approximately 5 and 300 mg/dL. The dry element is nearly equally sensitive to different proteins resulting in an accuracy that is suitable for its intended use, and better than the prior art solution and dry element-based assays. A major interference due to the presence of wide and varied bicarbonate levels in urine specimens has been overcome by the addition of glycolic acid in the dry element employing the pyrocatechol-molybdate chemistry. Other hydroxycarboxylic acids, such as those disclosed above, will have a similar effect, whether incorporated into the element or added with the sample. These two very different and unexpected findings have provided a sensitive and robust dry assay element, particularly suitable for the quantification of total protein in liquid samples.

The following examples are given to illustrate the scope of this invention. Because these examples are given for illustrative purposes only, the invention embodied therein should not be limited thereto. Except where noted, all reagents and equipment were obtained from commercial sources.

Examples 1–4 below, describe the results of experiments comparing analytical detection sensitivity and replicate precision of elements comprising different indicator dyes.

EXAMPLE 1

PYROCATECHOL VIOLET

Pyrocatechol violet was coated at 0.12 g/m$^2$ in the reagent layer comprising additionally, 12 g/m$^2$ of the acrylamide polymer having the following composition (poly (acrylamide-co-N-vinyl-2-pyrrolidone, 50:50 weight ratio)), hereinafter designated polymer AVP, the surfactant Zonyl FSN (0.36 g/m$^2$) and 5.9 g/m$^2$ of succinic acid (pH 2.5) as buffer, ammonium molybdate (0.18 g/m$^2$) and potassium oxalate at 0.15 g/m$^2$. A bead spreading layer (having the composition described below and as described in U.S. Pat. No. 4,258,001) was used. Between the spreading layer and reagent layer was a poly(N-vinyl-2-pyrrolidone) sub layer. The element was cut into squares 1 centimeter on an edge and mounted into slides. A Johnson & Johnson Clinical Diagnostic slide analyzer was used to spot the slide element with the solution comprising protein, to incubate the slide and to read reflectance density, Dr. This method of evaluating elements allows the practitioner to test many elements and to obtain replicate measurements conveniently. Any other method of spotting, incubating and measuring the optical signal will also be suitable for evaluating dry elements. The element structure is shown below:

| PYROCATECHOL VIOLET ELEMENT | |
|---|---|
| Spreading Layer 30 μm beads | Copoly(vinyltoluene methacrylic acid) |
| Sub Layer | Poly(N-vinyl-2-pyrrolidone) Copoly(acrylamide-co-N-vinyl-2-pyrrolidone) (50:50)$_{wt}$ Pyrocatechol violet |
| Reagent Layer | Succinic acid Ammonium molybdate Potassium oxalate Zonyl FSN |
| Support /////////////////////////////////////////// | |

Dr was measured at 670 nm. Table 1 below shows the results obtained using the pyrochatechol element described above. The fluids comprising the protein were prepared by adding a known weight of human serum albumin to a known volume of an aqueous solution of 0.15 M sodium chloride to obtain fluids having the albumin concentrations indicated in Table 1. An aliquot (10 uL) of the fluid comprising albumin was spotted onto the spreading layer of the element. The spotted element was then incubated for 5 minutes at 37° C. The reflectance density was then measured. The measured Dr is an average (<DR>) of 6 replicate measurements (n=6). %CV is the coefficient of variation about the average Dr:

TABLE 1

| HSA (mg/dL) | <Dr> | % CV |
|---|---|---|
| 10 | 1.022 | 4.8 |
| 50 | 1.209 | 1.0 |
| 100 | 1.370 | 2.3 |
| 150 | 1.489 | 1.9 |
| 300 | 1.732 | 4.7 |

The detection sensitivity of the pyrochatechol element as measured by the change in reflectance density (ΔDr=0.710) between 10 and 300 mg/dL albumin is very good. The %CV's are relatively small, indicative of good replicate precision.

EXAMPLE 2

PYROGALLOL RED

Pyrogallol red was coated at 0.18 g/m$^2$ in a barium sulfate spreading layer as described in U.S. Pat. No. 3,992,158. Surfactant TRITON X-100 (0.001 g/m$^2$), tartaric acid (6.0 g/m$^2$, pH 2.5) and oxalic acid, 2 g/m$^2$, were coated in the reagent layer using the homopolymer of acrylamide, polyA (having an average molecular mass of 100,000 daltons) at a coverage of 10 g/m$^2$. Ammonium molybdate was coated at 0.9 g/m$^2$ in the barium sulfate spreading layer. A sub layer of poly(N-isopropylacrylamide) was coated between the spreading layer and the reagent layer. The structure of the element is shown below:

| PYROGALLOL RED ELEMENT | |
|---|---|
| Spreading Layer | Barium Sulfate Pyrogallol Red Ammonium Molybdate |
| Sub Layer | Poly(N-isopropylacrylamide) Polyacrylamide (polyA) |
| Reagent Layer | Tartaric acid Oxalic Acid TRITON X-100 |
| Estar Support /////////////////////////////////////////// | |

Several buffers were coated at pH 2.5, however, tartaric acid provided the most linear response (at 540 nm) over the protein concentration range tested. The experimental protocol was identical to that described for the pyrocatechol violet element except that Dr was measured at 540 nm. The results (n=6) are shown in Table 2.

TABLE 2

| HSA (mg/dL) | <Dr> | % CV |
|---|---|---|
| 100 | 0.281 | 5.0 |
| 50 | 0.327 | 4.9 |
| 150 | 0.363 | 7.1 |
| 300 | 0.382 | 4.4 |

The change in Dr over the tested albumin concentration range using the pyrogallol red element is 0.101, thus, the detection sensitivity is less than that obtained with the pyrocatechol violet element. The %CV's are small but somewhat greater than that observed using the pyrocatechol violet element.

EXAMPLE 3

BROMOPYROGALLOL RED ELEMENT

Bromopyrogallol red was coated at 0.24 g/m$^2$ in a reagent layer comprising 12 g/m$^2$ of the polyacrylamide vehicle, designated hereinafter as polymer AAM, poly(acrylamide-co-N-(3-acetoacetamidopropyl)methacrylamide) 95:5 weight ratio). Surfactant TRITON X-165 (0.20 g/m), malonic acid (8.0 g/m$^2$, pH 2.5) and ammonium molybdate (0.4 g/m$^2$) were also coated in the AAM layer. A barium sulfate spreading layer was coated over a poly(N-isopropylacrylamide) sublayer. The structure of the element comprising a barium sulfate spreading layer is shown below.

| BROMOPYROGALLOL RED ELEMENT | |
|---|---|
| Spreading Layer | Barium Sulfate |
| Sub Layer | Poly(N-isopropylacrylamide) |
| | Poly(acrylamide-co-N-(3- |
| | Bromopyrogallol red |
| Reagent Layer | Malonic acid |
| | Ammonium molybdate |
| | Potassium oxalate |
| | Bisvinylsulfonylmethyl ether (BVSME) |
| Estar base ///////////////////////////////////////////////// | |

The bromopyrogallol element was evaluated as described above for the elements comprising pyrochatechol and pyrogallol red indicator dyes. Data from evaluation of the bromopyrogallol (n=6) element is found in Table 3.

TABLE 3

| HSA (mg/dL) | <Dr> | % CV |
|---|---|---|
| 10 | 1.482 | 86.1 |
| 50 | 1.487 | 20.6 |
| 100 | 1.547 | 11.3 |
| 300 | 1.660 | 2.6 |

The change in Dr over the albumin concentration range is 0.178, which, therefore, provides less detection sensitivity than the pyrocatechol violet element. The %CV's are large, indicative of significant replicate imprecision.

EXAMPLE 4

GALLEIN

Gallein was coated at 0.12 g/m$^2$ in a barium sulfate spreading layer. Surfactant TRITON X-165 (0.2 g/m$^2$), malonic acid (8.0 g/m$^2$, pH 2.5) and oxalic acid (2.5 g/m$^2$) were coated in the copolymer, designated hereinafter as polymer AVP, having the molecular composition poly(acrylamide-co-N-vinyl-2-pyrrolidone)(50:50)$_{wt}$ at 10.0 g/m$^2$ to form a buffer layer. Ammonium molybdate (0.90 g/m$^2$) and surfactant TRITON X-100 (1 g/m$^2$) were coated in the barium sulfate layer spreading layer in addition to dye. The structure of the element is shown below.

| GALLEIN ELEMENT | |
|---|---|
| | Barium Sulfate |
| Spreading Layer | Gallein |
| | Ammonium molybdate |
| | TRITON X-100 |
| Sub Layer | Poly(N-isopropylacrylamide) |
| | Poly(acrylamide-co-N-vinyl-2- |
| | pyrrolidone) (50:50)$_{wt}$ |

-continued

| GALLEIN ELEMENT | |
|---|---|
| Buffer Layer | Malonic acid |
| | TRITON X-165 |
| | Oxalic acid |
| Estar Support ///////////////////////////////////////////////// | |

The gallein element was evaluated as described above for the other elements (n=6) and Dr was measured at 550 nm. The results are provided in Table 4:

TABLE 4

| HSA (mg/dL) | <Dr> | % CV |
|---|---|---|
| 10 | 0.541 | 85.7 |
| 50 | 0.569 | 20.3 |
| 100 | 0.565 | 93.1 |
| 300 | 0.580 | 19.5 |

The change in Dr over the albumin concentration range is 0.039, providing considerably reduced detection sensitivity compared with the pyrocatechol violet element. The %CV's are quite large, and indicative of significant replicate imprecision.

In this example, the effect of different reagent layer polymer vehicles on the determination of different protein types using dry analytical elements comprising pyrocatechol violet, the preferred dye, and ammonium molybdate were tested. The polymers compared in this experiment were polyA (having a mass average molecular mass of approximately 120,000 daltons), (poly(acrylamide-co-N-vinyl-2-pyrrolidone, 50/50 weight ratio)(polymer AVP) and a polymer having the molecular composition (poly(acrylamide-co-acrylic acid, 90/10 weight ratio)hereinafter designated as polymer PAA. The spreading layer, in all cases, was barium sulfate as described in the aforementioned U.S. Pat. No. 3,992,156. The polymers were coated at the same dry coverage (12 g/m$^2$). Solutions containing protein were prepared by adding a known weight of purified human protein of interest, including IgG, retinol binding protein and Kappa light chain, to a known volume of an aqueous solution containing 0.15 M sodium chloride. The elements were formulated into slides as mentioned above. Calibration of the assay was perfomed using the solutions containing purified human albumin (hereinafter referred to as calibrator fluids). A 10 μL aliquot of each solution containing 100 mg/dL of the test protein was spotted individually on separate dry analytical (slide) elements. The reflection density at 670 nanometers was measured after 5 minutes incubation of the slide at 37° C. The level of total protein in the sample was calculated from the measured reflection density and assay calibration using the aforementioned calibrator fluids. The results are shown in Table 5.

TABLE 5

Effect of Polymer Type on Protein Reactivity

| Polymer | Albumin mg/dL | Kappa light chain mg/dL | Lambda light chain mg/dL | IgG mg/dL | Retinol Binding Protein mg/dL | Alpha 1 microglobuln mg/dL |
|---|---|---|---|---|---|---|
| AVP | 100 | 33 | 33 | 64 | 62 | 44 |
| polyA | 100 | 44 | 52 | 73 | 73 | 66 |
| PAA | 100 | N.D.** | 34 | 59 | N.D. | N.D. |

**Not Done

The data in Table 5 show that the polymer affects the interaction of pyrocatechol and molybdate ion with proteins. polyA, in particular, acts to reduce the difference in observed Dr among the protein types, and therefore, the estimated protein concentration determined with respect to calibration using fluids comprising human albumin. This resulted in protein concentration estimates near to the expected 100 mg/dL based on the amount of protein added to the fluid. It was evident that the best performance, that is, the minimum dependence of the measured signal with respect to the type of protein tested, was provided by polyA.

EXAMPLE 6

In this example, the effect of glycolic acid on bicarbonate interference was evaluated. Glycolic acid was precoated in the reagent layer which also comprised polyA at 12 g/m$^2$. Glycolic acid was coated in the reagent layer at the levels indicated in Table 6. To a sample of pooled human urine was added sodium bicarbonate to obtain a final bicarbonate concentration of either 100 mM or 200 mM (final pooled urine sample pH=8.5 in both cases). The pH was not adjusted to the final observed value, but was that which resulted after bicarbonate addition. The total protein of the untreated urine pool control was 18 mg/dL (determined using a BIOTROL™ kit for measurement of total protein, which is a solution-based assay using pyrogallol red/ ammonium molybdate dye binding methodology available from Merck Biotrol Diagnostics, Exton, Pa. 19341; catalog no. A01217U). The reflection densities were measured as in Example 5 above, and total protein concentration was estimated using the measured Drs after calibration of the assay elements using fluids comprising human albumin as calibrator fluids as in Example 5. The protein estimate obtained for the control urine was subtracted from the protein estimate obtained for the bicarbonate treated urine samples. The data are shown in Table 6.

TABLE 6

Effect of glycolic acid on bicarbonate interference
Protein concentration difference between bicarbonate treated and bicarbonate free control

| Glycolic Acid | Bicarbonate | |
|---|---|---|
| g/m$^2$ | 100 mM | 200 mM |
| 0 | 35 | 110 |
| 0.125 | 22 | 77 |
| 0.25 | 13 | 54 |
| 0.375 | 8 | 30 |
| 0.5 | 4 | 20 |
| 0.75 | N.D. | 13 |
| 1.0 | N.D. | −2 |

(N.D. = not determined)

Bicarbonate acts to produce an optical signal that mimics protein. For example, in the absence of glycolic acid, the estimated protein concentration of a urine specimen having a bicarbonate concentration of 200 mM would be about 110 mg/dL greater than the actual level. As shown in Table 6, glycolic acid dramatically reduces the effect due to bicarbonate. Glycolic acid (or other suitable hydroxycarboxylic acids, as described earlier) could be added directly to the dry analytical element as in Example 6, or alternatively, added to the sample prior to contacting the dry analytical element with the sample. The useful concentration range of glycolic acid coated in an element is between approximately 0.125 and 2.0 g/m$^2$. Preferrably the range is 0.125 to 1.5 g/m$^2$, and a more preferred range is 0.25 to 1.25 g/m$^2$. The structure of the preferred dry analytical element is shown below:

| Spreading Layer | Barium Sulfate |
|---|---|
| Sub Layer | Poly(N-isopropylacryamide) |
| | Polyacrylamide (polyA) |
| | Glycolic Acid |
| | Pyrocatechol Violet Dye |
| Reagent/Buffer Layer | Ammonium Molybdate |
| | Potassium Oxalate |
| | Zonyl-FSN Surfactant |
| | Malonic Acid Buffer, pH = 2.5 |
| | Support |

The above experiments and examples are given to illustrate the scope and spirit of the present invention. These embodiments and examples will make apparent to those skilled in the art, other embodiments and examples. These other embodiments and examples are within the contemplation of the present invention; therefor, the instant invention should be limited only by the appended claims.

What is claimed is:

1. A dry analytical element for the determination of protein, said element comprising:
    (A) a porous spreading layer;
    (B) one or more additional layers comprising:
        (i) a dye capable of reacting with protein and molybdate ion to produce a change in spectral absorption or reflection density of said dye;
        (ii) a molybdate salt; and
        (iii) a polymer comprising acrylamide,
            wherein said dye, said molybdate salt and said polymer comprising acrylamide may be present together in the same layer or be present in any combination or individually in separate layers of said element;
    (C) a support.

2. The dry analytical element of claim 1, wherein said dye is selected from the group consisting of pyrocatechol violet, pyrogallol red, bromopyrogallol red and gallein.

3. The dry analytical element of claim 2, wherein said dye is pyrocatechol violet.

4. The dry analytical element of claim 1, wherein said molybdate salt is ammonium molybdate.

5. The dry analytical element of claim 1, wherein said polymer comprising acrylamide is selected from the group consisting of polyA, polymer AVP, polymer PAA and polymer AAM.

6. The dry analytical element of claim 5, wherein said polymer is polyA having a molecular mass range of between 100,000 and 150,000 daltons.

7. The dry analytical element of claim 1, wherein said dye is pyrocatechol violet, said molybdate salt is ammonium molybdate, and said polymer comprising acrylamide is polyA having a molecular mass range of between 100,000 and 150,000 daltons.

8. The dry analytical element of claim 7, wherein said porous spreading layer comprises barium sulfate.

9. A method for measuring protein comprising:
(A) combining a fluid suspected of containing protein with a hydroxycarboxylic acid having the general structural formula:

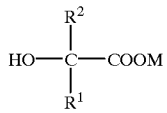

wherein $R^1$ and $R^2$ are independently H, —$CH_3$, —$CH_2CH_3$ or —$CH_2OH$,
and M is H, or a positively charged metal or non-metal counterion,;
(B) contacting said fluid comprising said hydroxycarboxylic acid and suspected of containing protein with a dry analytical element, said element comprising:
(a) a porous spreading layer;
(b) one or more additional layers in fluid contact with said porous spreading layer, comprising:
(i) a dye that is capable of reacting with protein and molybdate ion to produce a change in spectral absorption or reflection density of said dye;
(ii) a molybdate salt;
(iii) a polymer comprising acrylamide,
wherein said dye, said molybdate salt and said polymer comprising acrylamide may be present together in the same layer or be present in any combination or individually in separate layers of said element;
(c) a support; and
(C) measuring a change in spectral absorption or reflection density of the dye as a measure of protein.

10. The method of claim 9, wherein said dye is selected from the group consisting of pyrocatechol violet, pyrogallol red, bromopyrogallol red and gallein.

11. The method of claim 10, wherein said dye is pyrocatechol violet.

12. The method of claim 9, wherein said molybdate salt is ammonium molybdate.

13. The method of claim 9, wherein said polymer comprising acrylamide is selected from the group consisting of polyA, polymer AVP, polymer PAA and polymer AAM.

14. The method of claim 13, wherein said polymer is polyA having a molecular mass range of between 100,000 and 150,000 daltons.

15. The method of claim 9, wherein said dye is pyrocatechol violet, said molybdate salt is ammonium molybdate and said acrylamide polymer is polyA having a molecular mass range of between 100,000 and 150,000 daltons.

16. The method of claim 15, wherein said porous spreading layer comprises barium sulfate.

17. A dry analytical element for the determination of protein, said element comprising:
(A) a porous spreading layer;
(B) one or more additional layers in fluid contact with said porous spreading layer, comprising:
(i) a dye that is capable of reacting with protein and molybdate ion to produce a change in spectral absorption or reflection density of said dye;
(ii) a molybdate salt;
(iii) a polymer comprising acrylamide;
(iv) an hydroxycarboxylic acid having the general structural formula:

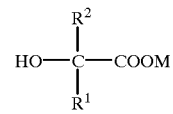

wherein $R^1$ and $R^2$ are independently H, —$CH_3$, —$CH_2CH_3$ or —$CH_2OH$,
and M is H, or a positively charged metal or non-metal counterion, and
wherein said dye, said molybdate salt, said polymer comprising acrylamide and said hydroxycarboxylic acid may be present together in the same layer or be present in any combination or individually in separate layers of said element; and
(C) a support.

18. The dry analytical element of claim 17, wherein said dye is selected from the group consisting of pyrocatechol violet, pyrogallol red, bromopyrogallol red and gallein.

19. The dry analytical element of claim 18, wherein said dye is pyrocatechol violet.

20. The dry analytical element of claim 17, wherein said molybdate salt is ammonium molybdate.

21. The dry analytical element of claim 17, wherein said polymer comprising acrylamide is selected from the group consisting of polyA, polymer AVP, polymer PAA and polymer AAM.

22. The dry analytical of claim 21, wherein said polymer is polyA having a molecular mass range of between 100,000 and 150,000 daltons.

23. The dry analytical element of claim 17, wherein said hydroxycarboxylic acid is selected from the group consisting of glycolic acid, 2-hydroxypropanoic acid, 2-methyl-2-hydroxypropanoic acid and salts thereof.

24. The dry analytical element of claim 23, wherein said hydroxycarboxylic acid is glycolic acid.

25. The dry analytical element of claim 17, wherein said dye is pyrocatechol violet, said molybdate salt is ammonium molybdate, said acrylamide polymer is polyA having a molecular mass range of between 100,000 and 150,000 daltons and said hydroxycarboxylic acid is glycolic acid.

26. The dry analytical element of claim 25, wherein said porous spreading layer comprises barium sulfate.

27. A method for measuring protein comprising:
(A) contacting a fluid sample suspected of containing protein with a dry analytical element comprising:
(a) a porous spreading layer;
(b) one or more additional layers in fluid contact with said porous spreading layer, comprising:
(i) a dye that is capable of reacting with protein and molybdate ion to produce a change in spectral absorption or reflection density of said dye;

(ii) a molybdate salt;
(iii) a polymer comprising acrylamide;
(iv) an hydroxycarboxylic acid having the general structural formula:

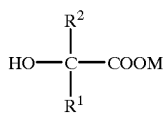

wherein $R^1$ and $R^2$ are independently H, —$CH_3$, —$CH_2CH_3$ or —$CH_2OH$,
and M is H, or a positively charged metal or non-metal counterion, and
wherein said dye, said molybdate salt, said polymer comprising acrylamide and said hydroxycarboxylic acid may be present together in the same layer or be present in any combination or individually in separate layers of said element;
(c) a support; and
(B) measuring a change in spectral absorption or reflection density of the dye as a measure of protein.

28. The method of claim 27, wherein said dye is selected from the group consisting of pyrocatechol violet, pyrogallol red, bromopyrogallol red and gallein.

29. The method of claim 28, wherein said dye is pyrocatechol violet.

30. The method of claim 27, wherein said molybdate salt is ammonium molybdate.

31. The method of claim 27, wherein said polymer comprising acrylamide is selected from the group consisting of polyA, polymer AVP, polymer PAA and polymer AAM.

32. The method of claim 31, wherein said polymer comprising acrylamide is polyA having a molecular mass range of between 100,000 and 150,000 daltons.

33. The method of claim 27, wherein said hydroxycarboxylic acid is selected from the group consisting of glycolic acid, 2-hydroxypropanoic acid, 2-methyl-2-hydroxypropanoic acid and salts thereof.

34. The method of claim 33, wherein said hydroxycarboxylic acid is glycolic acid.

35. The method of claim 27, wherein said dye is pyrocatechol violet, said molybdate salt is ammonium molybdate, said acrylamide polymer is polyA having a molecular mass range of between 100,000 and 150,000 daltons, and said hydroxycarboxylic acid is glycolic acid.

36. The method of claim 35, wherein said porous spreading layer comprises barium sulfate.

* * * * *